United States Patent
Gelman

Patent Number: 5,807,329
Date of Patent: Sep. 15, 1998

[54] DISPLACEABLE CATHETER DEVICE

[76] Inventor: Martin L. Gelman, 188 Elm St., Hopkinton, Mass. 01748

[21] Appl. No.: 643,772

[22] Filed: May 7, 1996

[51] Int. Cl.$^6$ ................................................ A61M 29/00
[52] U.S. Cl. ............................ 604/96; 604/102; 604/264
[58] Field of Search ............................... 604/93, 96, 102, 604/103, 266, 264, 268, 280; 606/191, 194

[56] References Cited

U.S. PATENT DOCUMENTS

| | | | |
|---|---|---|---|
| 2,819,718 | 1/1958 | Goldman | 128/350 |
| 4,157,094 | 6/1979 | Patel | 128/349 |
| 4,217,903 | 8/1980 | Witherow | 428/349 B |
| 5,059,177 | 10/1991 | Towne et al. | 604/96 |
| 5,338,297 | 8/1994 | Kocur et al. | 604/96 |
| 5,453,076 | 9/1995 | Kiyata et al. | 600/18 |

*Primary Examiner*—Corrine M. McDermott
*Assistant Examiner*—Cris L. Rodriguez
*Attorney, Agent, or Firm*—Scott B. Garrison; Lambert & Garrison PLLC

[57] ABSTRACT

A displaceable ballooning catheter for displacement off an occluding membrane within a patient's body. The device contains the normal inflow and outflow ports of typical catheters but in addition contains a fluid filled balloon that upon inflation will move away from a blood vessel wall thereby ensuring adequate flow into the catheter during hemodialysis. The balloon is adaptable to other methods of catheterization such as peritoneal dialysis and pressure monitoring because the balloon is capable of moving the catheter tip enough to situate the catheter in its optimum location for the procedure intended.

4 Claims, 4 Drawing Sheets

DISPLACEABLE CATHETER DEVICE

BACKGROUND OF THE INVENTION

The present invention relates to the field of catheterization. More particularly, it relates to an improvement capable of adaptation to a wide range of catheters thereby permitting manipulation of a catheter internal to a patient's body without further invasive procedures on the part of a physician. The invention is especially well-suited for use in the dialysis field, however it would add significant advantages to other catheterization procedures as well.

Currently approximately 190,000 patients undergo dialysis therapy, 85 percent of which are on hemodialysis, the remaining 15 percent are on peritoneal dialysis. Hemodialysis, the process of removing toxic waste products from the blood by convection and diffusion, has been available for patients with kidney failure for over 30 years. Widespread use of the process began in the United States in 1972 with the passage of the End-Stage Renal Disease Program under Medicare legislation. Whereas peritoneal dialysis is a similar process in which toxic substances are also removed by a diffusion process utilizing a surgically placed abdominal catheter to allow inflow and outflow of dialysate solution into and out of the abdomen.

In hemodialysis, subcutaneous connections between arteries and veins are usually created using either native vessels (fistulae) or synthetic graft material such as Gortex, polyurethane, PTFE, silicone, and others. Such connections allow for needle cannulation to support the hemodialysis process. Once access is gained to the circulatory system, the blood is pumped into a filter device composed of numerous hollow strands or fibers which are then bathed with cleansing dialysate solution to remove the high concentration of waste products in the blood by osmotic diffusion.

Oftentimes grafts or fistulae cannot be created early on in the course of dialysis if required urgently. Additionally, if the grafts or fistulae fail due to clotting, infection, or luminal narrowing then alternative access to the blood is achieved through the introduction of a catheter. A variety of problems are associated with the subcutaneous introduction of a hemodialysis catheter including septicaemia, thrombosis, hemorrhage, catheter tip migration and leakage as well as other complications. One major problem frequently encountered is that of an initial or subsequent poor blood flow rate through the catheter resulting in inadequate dialysis exchange. A common cause of this problem is due to occlusion of the catheter inlet because the slight suction created at the catheter inlet has the tendency to cause the catheter itself to migrate toward the blood vessel wall. In peritoneal dialysis, the peritoneal catheter can also lodge against the abdominal wall, omentum, or the intraperitoneal structures limiting the outflow of peritoneal dialysate solution.

Until Raulerson, U.S. Pat. No. 4,037,599, separate catheters were required for inflow and outflow of fluids to a patient. Raulerson disclosed a single dual lumina catheter which allowed arterial inflow and venous outflow through separate lumens of a single catheter. This allowed for blood flow through a single catheter thereby eliminating the necessity of a single-needle machine and the heightened possibility of blood recirculation in the patient. Dual lumen catheters are designed typically in either one of two configurations, coaxial or side-by-side. Coaxial type catheters usually comprise an inner disposable cannula which slidingly engages an outer fixed cannula. Side-by-side type catheters are typically configured in a "D" type design. The "D" type design comprises a single cannula axially divided by a noncommunicating wall. This wall isolates the cannula into two separate "D" shaped channels.

Both designs have certain disadvantages to their use. The disadvantage of "D"-type catheters is that because of the noncommunicating wall, arterial inflow and venous outflow must occur on opposite sides of the cannula. This does not eliminate the slight vacuum on the arterial inflow lumen, referenced above, resulting in the catheter migrating toward the side wall of the blood vessel causing catheter occlusion. To avoid this problem, physicians routinely perform various manipulations to the catheter designed to free the catheter of the occlusion. Common methods are rotation of the catheter on its axis to free the inflow port, pulling the catheter back, or if all else fails reversing the flow using the arterial side port of the catheter as the venous outflow limb and the original venous channel as the arterial inlet. These manipulations heighten the possibility of adverse consequences to both the catheter and the patient. Additionally, the last manipulation results in significant admixing of inflow and outflow of blood thereby compromising the efficiency of the dialysis treatment.

Coaxial catheters are not normally subject to this localized vacuum effect because the arterial intake ports are located around the circumference of the entire outer cannula. However, one disadvantage of older versions of coaxial type catheters were that the inner cannula had to be withdrawn and disposed of after each and every dialysis treatment. The frequency of changing the inner cannula increased the probability of catheter leakage because some means or method of withdrawing the inner cannula without losing significant blood from the patient must be designed into the catheter. This means or method, usually a valve, is where such leakage frequently originated and in most cases is simply accepted as being unavoidable.

Markel et. al, U. S. Pat. No. 5,053,004, a coaxial type catheter purports to eliminate this design deficiency by integrally mounting the inner cannula to the outer cannula. This feature eliminates the ability and necessity of withdrawing the inner cannula from the catheter for each dialysis treatment. Although Markel would seem to eliminate a great disadvantage to the use of coaxial catheters, it does nothing to address the problem of blockage of one or more arterial intake ports. In the event that blockage were to occur, the coaxial catheter would exhibit the same problem that the "D" type catheter possesses, the problem of a localized vacuum developing. Once flow is partially occluded and inflow hemodynamics are impacted sufficiently, the dialysis treatment suffers.

In spite of the existence of the above prior art catheters, no catheter contemplates a solution to the problem of blockage of an inflow port thereby affecting catheter performance, specifically by catheter migration internally within the patient. The present invention contemplates a solution wherein an expandable balloon is placed in proximity to the inflow port. The balloon upon inflation, would displace the catheter from the cause of the occlusion whether it be a vessel wall in hemodialysis or omentum, bowel or any internal membrane in peritoneal dialysis. The use of ballooning elements in catheters per se is not new. However, no ballooning catheters possess the capabilities of the present invention.

For instance, angioplasty catheters contain ballooning elements for the purpose of dilating stenotic or narrowed vessels commonly associated with cardiovascular or peripheral vascular diseases. Angioplasty balloon type catheters are designed for arterial dilatation and would not operate to displace the catheter tip off an arterial wall. Rather, if a physician attempted to use an angioplasty balloon type catheter for the present problem, the balloon would contact the interior circumference of the vessel wall and distend the vessel wall radially outward. Additionally, this type of catheter would contribute to blockage because while the balloon was in an inflated embodiment blood flow through the artery would be occluded completely.

Another ballooning catheter is a urinary bladder catheter. Such a catheter is designed to be fed via a smaller access passage to some larger body cavity. This catheter is specifically designed to be inserted into the patient's bladder via the urethra. A balloon is provided having the capability to inflate sufficiently to prevent it from being withdrawn from the bladder, thereby anchoring the catheter inflow and outflow ports well within the bladder cavity. Another anchoring type catheter is an endotracheal tube catheter. Such a catheter is designed to anchor the catheter in the patient's trachea between the patient's larynx and carina and works similar to the urinary bladder catheter.

A final catheter which uses a ballooning element is a gastrointestinal catheter. This type of catheter makes use of a balloon at the end designed to contain a heavy fluid, such as mercury. The filled balloon and catheter combination are designed to be inserted into the patient's stomach where normal peristaltic action of the patient's gastrointestinal muscles causes the catheter to migrate to the location desired by the physician. None of these catheters could be used or modified sufficiently to remedy the problem which the inventor herein has solved. What is needed is a displaceable catheter device capable of permitting a physician to manipulate the catheter to avoid inflow port occlusion without necessitating the use of further invasive procedures upon the patient.

SUMMARY OF THE INVENTION

This invention proposes a solution to the above referenced problem. One such invention relates to an otherwise dual lumen catheter further possessing at least one additional or third lumen. The third lumen channels along an axial line of the catheter similar to the arterial and venous cannulae, but this third lumen does not communicate fluids to the patient. The third lumen would terminate in a balloon wall. The balloon wall is located in close proximity to at least one arterial inflow port. The third lumen and balloon would contain a non-toxic, benign or beneficial fluid such as saline solution. When some minimal amount of pressure is applied to the third lumen, the balloon inflates sufficiently to push the catheter off the blood vessel wall thereby improving blood flow through the catheter.

One embodiment is easily adapted for "D" type catheters and another embodiment is easily adapted for coaxial catheters. In either case, the expandable balloon located next to the arterial side port would push the catheter off the side wall of the vessel where the catheter lies. This would allow correct catheter hemodynamics and would avert the need to change the catheter resulting in hemodynamic compromise.

Additionally, the present invention is readily adapted to use in other styles of catheters, such as triple or multi-lumen catheters, port-a-caths, pulmonary artery or Swan-Ganz catheters, arterial lines, and the aforementioned peritoneal catheter. The displaceable ballooning member ensures that these catheters remain within their proper functional positions. Multi-lumen catheters are similar to dual lumen versions but they have at least one additional lumen in fluid communication with a patient. The additional lumen is used to administer medications, parenteral nutrition, blood drawing and the like. The same concerns exist for these catheters as do dual lumina models.

Port-a-Caths are semi-permanent intravenous lines used for the prolonged infusion of intravenous fluids such as medications and parenteral nutrition. Additionally, such devices are used in patients who require frequent blood monitoring over extended periods of time. Such catheters often require removal and relocation, both necessitating surgical procedures, in the event of complications. Providing the physician with a means to manipulate the catheter increases the likelihood of eliminating the complications associated with blockage of the catheter without resorting to surgery.

Pulmonary artery or Swan-Ganz catheters and arterial lines are used to measure pressures, the former to monitor atrial pressure, the latter to monitor continuous arterial pressure. Accuracy of these catheters is dependent upon proper positioning. Having a means to manipulate these catheters to ensure proper positioning increases the likelihood of accurate measurements.

Peritoneal catheters can be improved by the addition of the ballooning element since the physician would not be required to resort to emetics or cathartics to cause convulsive displacement of the catheter inflow port off the occluding membrane. Additionally, the slight weight of the fluid in the balloon will prevent the catheter inflow ports from rising above the surface of the peritoneal stent fluid, resulting in the catheter losing suction.

All of the envisioned catheters adapted for use with the present invention will be imbued with prolonged life, a reduction in malfunction, decreased costs, and increased patient comfort and safety. Many of the 190,000 patients in the USA and the 500,000–600,000 patients worldwide require dialysis catheters occasionally in their dialysis careers. Many of these catheters fail due to hemodynamic compromise and this new displaceable catheter should assist in minimizing some of the complications associated with the hemodialysis and other catheterization processes.

It is therefore an object of this invention to provide a catheter device which allows a physician to manipulate the catheter internal to a patient's body by inflating or deflating a balloon means contained within the catheter.

It is another object of the present invention to overcome the problems of catheter migration and occlusion of the catheter ports located within the patient's body.

It is an object of this invention also to provide a catheter device which eliminates partial occlusion of the arterial inflow port resulting from the localized vacuum effect associated with the suction process.

It is another object to provide a catheter device which once properly placed does not require constant manipulation to maintain adequate blood hemodynamics through the catheter.

It is another object of this invention to provide a catheter device which reduces the likelihood of patient discomfort associated with the removal and subsequent relocation of a catheter by eliminating the need to relocate the catheter for reasons associated with partial occlusion of the catheter by the blood vessel wall.

It is another object of this invention to provide an improved catheter device for use in hemodialysis, peritoneal dialysis, and other dialysis procedures.

It is yet another object of this invention to provide a catheter which overcomes the deficiencies of prior art catheters but is still economical to produce and use.

BRIEF DESCRIPTION OF THE DRAWINGS

The novel features considered characteristic of the invention are set forth in the appended claims. The invention itself, however, both as to its construction and its method of operation, together with additional objects and advantages thereof, will best be understood from the following description of the specific embodiments when read and understood in connection with the accompanying drawing.

DETAILED DESCRIPTION OF THE PREFERRED EMBODIMENT

Figure 1:
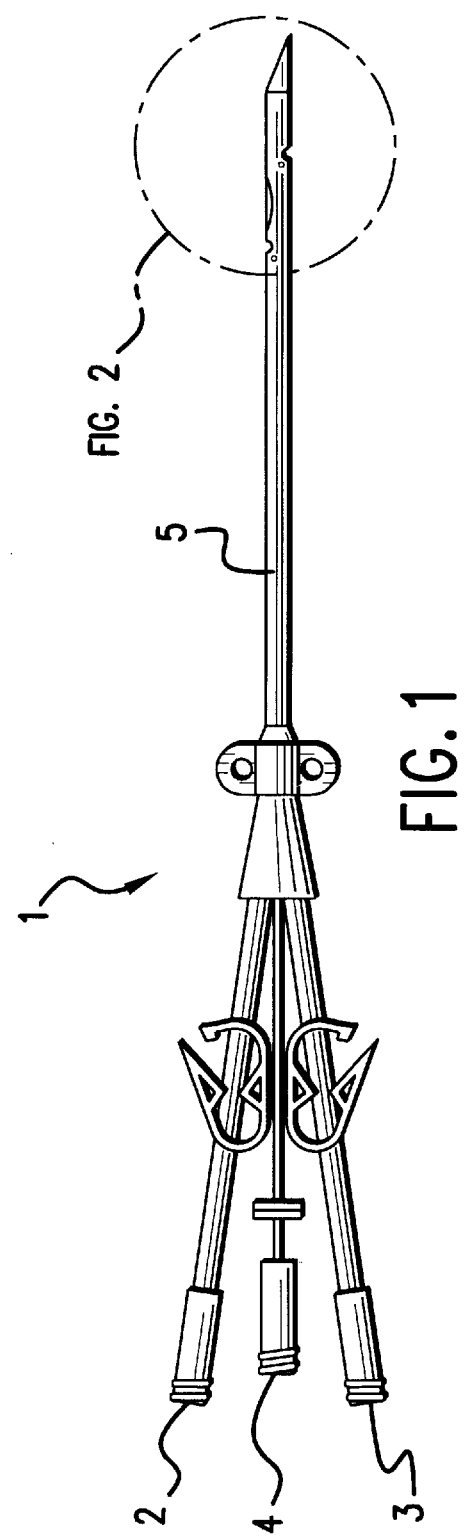
FIG. 1 is a front plan view of the catheter device of the present invention.

With reference to FIG. 1, a preferred embodiment of a catheter device is indicated generally at 1 depicting an arterial lumen 2, a venous lumen 3, and a saline lumen 4. Each of lumens 2, 3 and 4 are formed from materials commonly used in the prior art manufacture of catheters and as such are not part of the present invention. Catheter tube 5 is also made of material commonly used to produce catheter tubes in the prior art and it does not form part of the present invention. The invention itself relates to the purpose saline lumen 4 promotes and the internal configuration of catheter 1 as best depicted in FIGS. 2 and 3.

Figure 2:
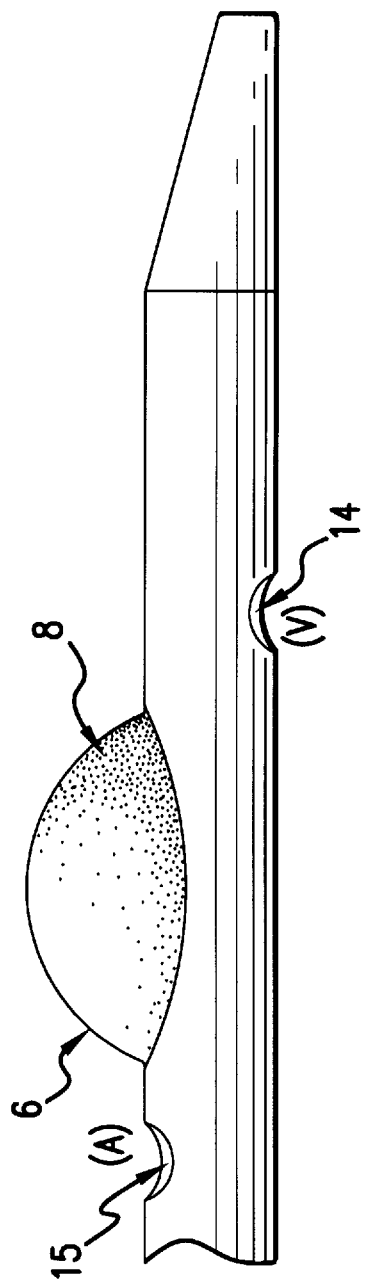
FIG. 2 is a partial detail view of the distal end of the catheter of FIG. 1.

FIG. 2 depicts balloon means 6 in an inflated embodiment. Balloon means 6 is connected to saline lumen 4 through cannula 7 as illustrated in FIG. 3 and as such saline contained within cannula 7 cannot enter a patient's body. Applying a positive pressure means to cannula 7 via lumen 4 such as by injecting saline into cannula 7 inflates balloon means 6 to the expanded embodiment. Likewise application of a negative pressure means or by equalizing cannula 7 pressure with catheter external ambient pressure by releasing or withdrawing saline from cannula 7 serves to deflate balloon means 6 thereby placing balloon means 6 in a nonexpanded embodiment. Balloon means 6 must be made of a hominine compatible material having at least the properties of minimal to no toxicity, high elasticity, low to no porosity and the capability of withstanding cyclic inflation and deflation without significant weakening of balloon wall 8. It is envisioned that silicone possesses the requisite qualities and as such will suffice.

Figure 3:
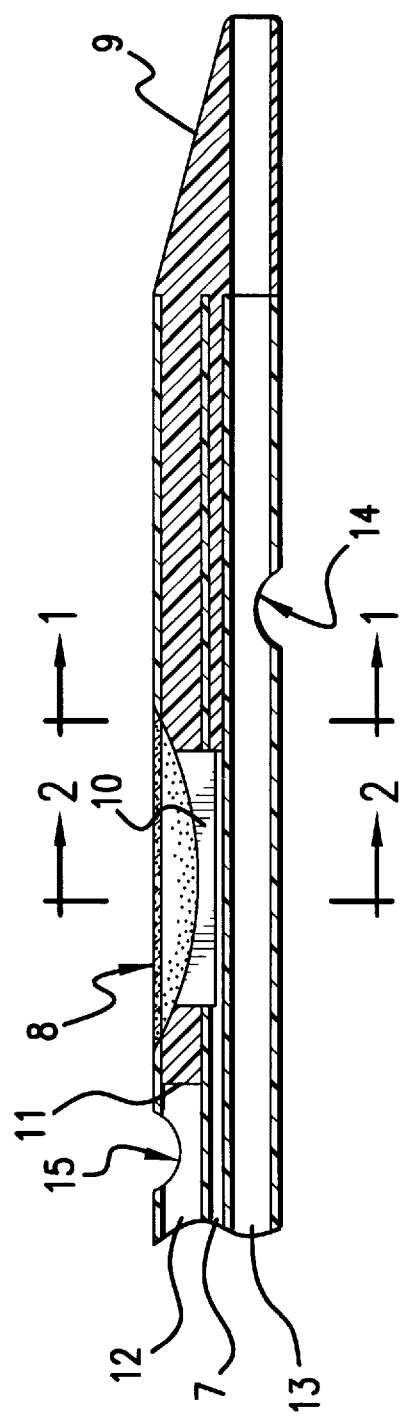
FIG. 3 is a partial cross-sectional view of the FIG. 2 view.
Figure 4:
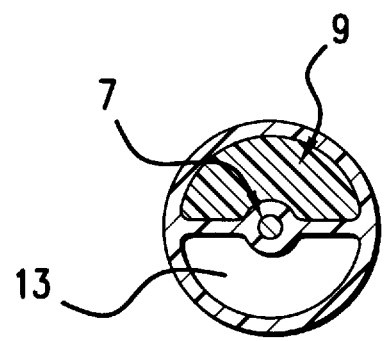
FIG. 4 is a sectional view along line 1—1 of FIG. 3 depicting an end plug in the arterial port of one embodiment of the present invention.
Figure 5:
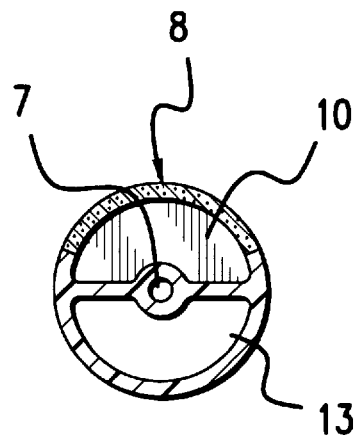
FIG. 5 is a sectional view along line 2—2 of FIG. 3 depicting the balloon wall of the present invention.

In the preferred embodiment, a "D" type catheter would be modified as follows to enable catheter tube 5 to form the present invention as depicted in FIG. 3. Arterial lumen 2 and saline lumen 4 are sealed at the distal end of catheter 1 by a first plug means 9 as depicted in FIG. 4. First plug means 9 seals cannulae 7 and 12 at the distal end of catheter 1 preventing saline from migrating beyond balloon chamber 10. Second plug means 11 seals cannula 12 between balloon chamber 10 and arterial inflow port 15 preventing blood from migrating beyond arterial inflow port 15 into balloon chamber 10. Plug material can be made from silicone, other hominine compatible materials or the catheter itself can be structurally designed to form the requisite chamber arrangement. Essentially venous cannula 13 which connects to venous lumen 3 is the only cannula to remain unmodified from prior art designs. Balloon chamber 10 is therefore open solely to saline lumen 4 by means of access to cannula 7. Balloon chamber 10 serves as a reservoir for saline and is noncommunicating with a patient's body by means of balloon wall 8 as shown in FIGS. 3 and 5. The preferred location of balloon chamber 10 is between arterial inflow port 15 and venous outflow port 14. Additionally, the preferred embodiment as reflected in the attached figures depicts a single arterial and single venous port. It should be noted, however, that a plurality of arterial or venous ports or both would work equally as well and may actually be desirable in certain cases.

Use of the present invention is simple. If in the opinion of a medical expert, the blood flow through catheter 1 is insufficient due to occlusion of arterial inflow port 15, balloon means 6 is expanded thereby displacing the catheter off the side wall of the vessel opening arterial inflow port 15. Expansion of balloon means 6 is accomplished by injecting saline solution into saline lumen 4. The saline exerts pressure onto balloon chamber 10 thereby expanding balloon means 6.

The invention is also suitable to coaxial type catheters and would work on the same principle. The only significant difference being the internal arrangement of balloon chamber 10 in relation to arterial cannula 12. One design configuration would allow the balloon means to expand circumferentially substantially around the entire radius of the catheter or alternatively to expand at one or more points around the radius of the catheter. The only requirement is that the saline cannula be noncommunicating with either the arterial and venous cannulae and only communicate with the balloon chamber thereby providing the balloon means with a means for expansion.

The two methods of making and using the device detailed above constitute the inventor's preferred embodiment and an alternate embodiment to the invention. The inventor is aware that numerous configurations are available which would provide the desired results. While the invention has been described and illustrated with reference to a specific embodiment, it is understood that these other embodiments may be resorted to without departing from the invention. Therefore the form of the invention set out above should be considered illustrative and not as limiting the scope of the following claims.

What is claimed is:

1. A catheter for dialysis treatment comprising:
   a catheter tube longitudinally divided by a dividing wall into a first semi-cylinder and a second semi-cylinder along a length, a proximal end in communication with an external environment, a distal end in communication with a patient internal environment,
   a first port near said distal end extending through a side wall of said catheter tube into said first semi-cylinder, a second port near said first port but closer to said proximal end of said catheter tube extending through said side wall into said second semi-cylinder, and a chamber between said first and second ports in communication with an external surface of said catheter tube and longitudinally aligned but not in communication with said second semi-cylinder;
   a balloon having an interior surface and an exterior surface disposed within said chamber, said balloon being inflatable over a range spanning from a first nonexpanded position to a second fully expanded position wherein said second fully expanded position is characterized by said balloon protruding outward from said chamber;

a cannula contained within said dividing wall and longitudinally extending between said proximal end of said catheter tube and said interior surface of said balloon; wherein said first semi-cylinder forms a cannula between said proximal end of said catheter tube and said first port, and said second semi-cylinder forms a cannula between said proximal end of said catheter tube and said second port; and said balloon when inflated cocks said catheter tube within said patient internal environment thereby displacing said distal end of said catheter tube enough to reduce occlusion of said second port.

2. The catheter of claim 1 wherein said catheter is suitable for hemodialysis.

3. The catheter of claim 1 wherein said catheter is suitable for peritoneal dialysis.

4. A catheter of the type associated with hemodialysis treatment comprising:

a catheter tube having a distal end and a side wall, said catheter tube for intravenous placement within a patient blood vessel;

a first and a second port through said catheter tube in communication with said side wall disposed proximate to said distal end;

a first and a second cannula each contained within said catheter tube, said first cannula in communication with said first port and said second cannula in communication with said second port, each of said first and said second cannulae capable of transferring a liquid between an external environment and said patient blood vessel;

a third cannula disposed within said catheter tube;

a chamber disposed within said catheter tube between said first and second ports proximate to at least one of said ports, said chamber longitudinally aligned with one of said ports but not the other along the length of said catheter tube;

a balloon means disposed within said chamber further having an internal surface and an external surface, said balloon means capable of receiving on said internal surface a liquid via said third cannula, whereby filling said balloon means with said liquid distends said external surface of said balloon means radially outward from that side of said catheter tube side wall containing said chamber causing said external surface of said balloon means to displacingly contact an internal wall of said blood vessel thereby cocking said catheter tube within said blood vessel and moving one of said ports from an occluded position to a non-occluded position.

\* \* \* \* \*